(12) United States Patent
Lin et al.

(10) Patent No.: US 7,901,877 B2
(45) Date of Patent: Mar. 8, 2011

(54) GENETIC MARKERS AND METHODS FOR DETECTING AND TREATING CANCERS

(75) Inventors: Chin-Tarng Lin, Taipei (TW);
Han-Chung Wu, Taipei (TW);
Dah-Yeou Huang, Taipei (TW)

(73) Assignee: National Taiwan University, Taipei (TW)

( * ) Notice: Subject to any disclaimer, the term of this patent is extended or adjusted under 35 U.S.C. 154(b) by 469 days.

(21) Appl. No.: 11/907,697

(22) Filed: Oct. 16, 2007

(65) Prior Publication Data
US 2009/0054363 A1 Feb. 26, 2009

(30) Foreign Application Priority Data

Aug. 23, 2007 (TW) ................................ 96131196 A

(51) Int. Cl.
*C12Q 1/00* (2006.01)
*G01N 33/574* (2006.01)
(52) U.S. Cl. .................. 435/4; 435/6; 435/7.1; 435/7.23
(58) Field of Classification Search .................. None
See application file for complete search history.

(56) References Cited

U.S. PATENT DOCUMENTS

| 2005/0043512 A1* | 2/2005 | Toda et al. ..................... 530/350 |
| 2008/0113360 A1* | 5/2008 | Riker et al. ....................... 435/6 |
| 2009/0047689 A1* | 2/2009 | Kolman et al. .............. 435/7.23 |

OTHER PUBLICATIONS

Ueda et al int. J. Cancer, vol. 120, p. 1704-11, 2007.*
Blaes et al., Ann Thorac Surg, vol. 69, p. 254-8, 2000.*
* cited by examiner

*Primary Examiner* — Misook Yu
*Assistant Examiner* — Lei Yao
(74) *Attorney, Agent, or Firm* — Birch, Stewart, Kolasch & Birch, LLP

(57) ABSTRACT

The present invention provides genetic markers, SOX5 and SPARC, for distant metastasis and poor prognosis of detection of the high risk potential for cancer patients. In addition, the present invention also provides a method to predict the risk potential for cancer patients with distant metastasis and poor prognosis. This method comprises obtaining a tissue sample from a patient; evaluating the expression levels of the SOX5 and/or SPARC genetic markers in the sample; and comparing the expression levels of genetic markers with those of non-cancerous tissues. The patient is determined to have the high risk of distant metastasis or poor prognosis when the expression level of SOX5 is higher, or when the expression level of SPARC is lower, than that of non-cancerous tissue. Furthermore, the identified genetic marker SOX5 and/or SPARC can also be used for cancer targeted therapy, because down regulation of SOX5 and/or up regulation of SPARC expression in NOD-SCID can retard tumor growth and inhibit cell proliferation, migration, invasion and metastasis.

7 Claims, 11 Drawing Sheets
(5 of 11 Drawing Sheet(s) Filed in Color)

A

B

A

B

A

B

GENETIC MARKERS AND METHODS FOR DETECTING AND TREATING CANCERS

BACKGROUND OF THE INVENTION

1. Field of the Invention

The invention relates to genetic markers to identify cancer patients who are at the high risk for developing distant metastasis or poor prognosis. The genetic markers can serve as target genes in cancer therapy including nasopharyngeal cancer, hepatic cancer, lung cancer, or uterine cervical cancer. The present invention further relates to a method for predicting a risk of distant metastasis and poor prognosis in cancer patients including nasopharyngeal cancer, liver cancer, lung cancer, or uterine cervical cancer.

2. The Prior Arts

The cancer mortality increased dramatically for the past twenty years in the world. Nasopharyngeal carcinomas (NPC) arise from the squamous epithelium lining the surface and crypts of the nasopharynx. According to World Health Organization, it accounts for 0.3% of malignancies in Europe and North America. However, it has a high incidence for Chinese in regions of southern China, Hong Kong, Taiwan, and Singapore. NPC appear to have a significant ethnic and geographical distribution. Recent studies have attributed the development of NPC to a complex interaction of genetic factors, environmental factors and viral infection. Some of the oncogenes and tumor suppressor genes may be mutated after long time accumulation, which causes the normal cells change to cancer cells.

The infection of Epstein-Barr virus was regarded as the main cause of NPC, which was based on studies of the genome or gene products of Epstein-Barr virus found in NPC tissues. However, that concentrated too much on Epstein-Barr virus found in NPC tissues.

Not all NPC cell lines contained Epstein-Barr virus, and only a fraction of cells were found to harbor Epstein-Barr virus in the positive cell lines. The results were in consistent with the biopsy specimens obtained from NPC patients. In addition, the non-transformed squamous metaplastic cells of nasopharyngx contain no Epstein-Barr virus. All these results show that Epstein-Barr virus is not the major cause for NPC development, which is also supported by the following facts: (1) the cells from samples of NPC cell line or NPC biopsy did not express receptors for Epstein-Barr virus; (2) part of the NPC cells from NPC biopsy expressed secretory component protein (SC protein), the receptor of IgA, but not the non-transformed squamous metaplastic cells in nasopharynx; (3) NPC cell line carrying IgA receptors can be infected by Epstein-Barr virus (EBV) through IgA anti-EBV-VCA, (4) the growth rate of NPC cells increased if infected with Epstein-Barr virus.

Recently, many genetic abnormalities in NPC tissues have been defined by genome-wide studies through the progress in molecular biology. It has been reported that the changes of tumor suppressor genes on chromosome 3p, 9p, 11q, 13q, 14q, and 16q and oncogenes on chromosome 8, 12 were important in NPC development. Many studies are focus on the alleles of the above mentioned chromosomes. For example, RASSFIA gene on chromosome 3p is regarded as a tumor suppressor gene for NPC. Only RASSFIA was studied deeply in the mechanism of NPC up to present. Nevertheless, the development of NPC is believed to have a multifactorial etiology, the main regulating mechanism remains to be elucidated.

The understanding of molecular mechanism in NPC development will contribute to the detection, prognosis, therapy and prevention of NPC. Though local control rate of NPC reached 90%, there is 30% to 40% of the late stage NPC patients having distant metastasis and local recurrences. The survival time was less than one year for those had distant metastasis. There is still no effective ways in predicting and treatment of distant metastasis of NPC. The studies in gene regulating mechanism of NPC and the identification of proper genetic markers for forecasting the risk of poor prognosis and distant metastasis, further to serve as target gene in cancer therapy is therefore important. In addition, application of the genetic markers of NPC in other cancers can be beneficial at the same time.

SUMMARY OF THE INVENTION

The present invention provides genetic markers for determining the development of distant metastasis and poor prognosis of a cancer. The genetic markers are SOX5 and/or SPARC, and the cancer is nasopharyngeal cancer, liver cancer, lung cancer, or uterine cervical cancer.

The expression of genetic marker SOX5 was increased, while the expression of SPARC was decreased in the cancer cells including nasopharyngeal cancer, liver cancer, lung cancer, or uterine cervical cancer in comparison with normal nasomucosal cells.

The present invention further provides a method for predicting a subject at a high risk for the development of distant metastasis or poor prognosis of a cancer. The method comprises: obtaining a sample from a cancer which is nasopharyngeal cancer, liver cancer, lung cancer, or uterine cervical cancer, and the sample is a tissue containing cancer cells; evaluating the expression levels of SOX5 and/or SPARC; comparing the expression levels of SOX5 and/or SPARC with a normal non-cancer tissue judging the increase in expression levels of SOX5 or decrease in expression levels of SPARC to indicate the high risk for the development of distant metastasis or poor diagnosis of a cancer.

The present invention further provides genes served for treating the cancer, wherein the genes are SOX5 and/or SPARC, and the cancer is nasopharyngeal cancer, liver cancer, lung cancer, or uterine cervical cancer. The proliferation rate and migration ability of cancer cells are weaker when the expression of gene SOX5 is inhibited; while the proliferation rate and migration ability of cancer cells are weaker, and the invasion ability is decreased when the expression of gene SPARC is overexpressed.

The present invention is further explained in the following embodiment, illustration and examples. The characteristics and advantages of the abovementioned objectives and other objectives are described in details as follows. Those examples below should not, however, be considered to limit the scope of the invention, it is contemplated that modifications will readily occur to those skilled in the art, which modifications will be within the spirit of the invention and the scope of the appended claims.

BRIEF DESCRIPTION OF THE DRAWINGS

The patent or application file contains at least one drawing executed in color. Copies of this patent or patent application publication with color drawing(s) will be provided by the office upon request and payment of the necessary fee.

The related drawings in connection with the detailed description of the present invention to be made later are described briefly as follows, in which.

and in NPC cell lines detected with Western blot analysis using tubulin, a house keeping protein, as the internal control B, Sox5 detected with immunostaining. a: negative control using normal chicken blood IgY antibody; b: immunostaining of Sox5 in the NPC cell line, using Sox5 antibody chicken IgY anti-Sox5; c: immunostaining of Sox5 in primary NPC biopsy specimens; d: immunostaining of Sox5 in biopsy specimen from NPC patient with distant metastatic nodule.

Figure 2:
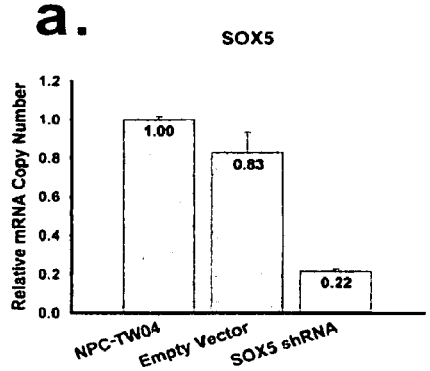
Figure 2:
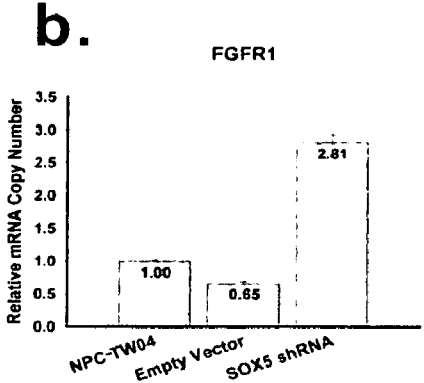
Figure 2:
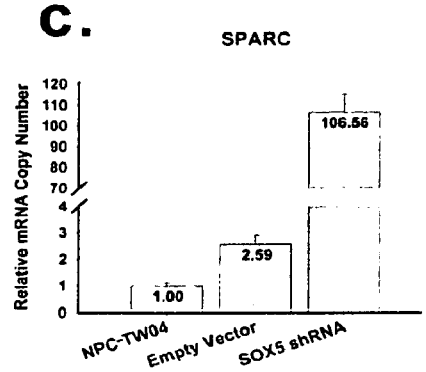
Figure 2:
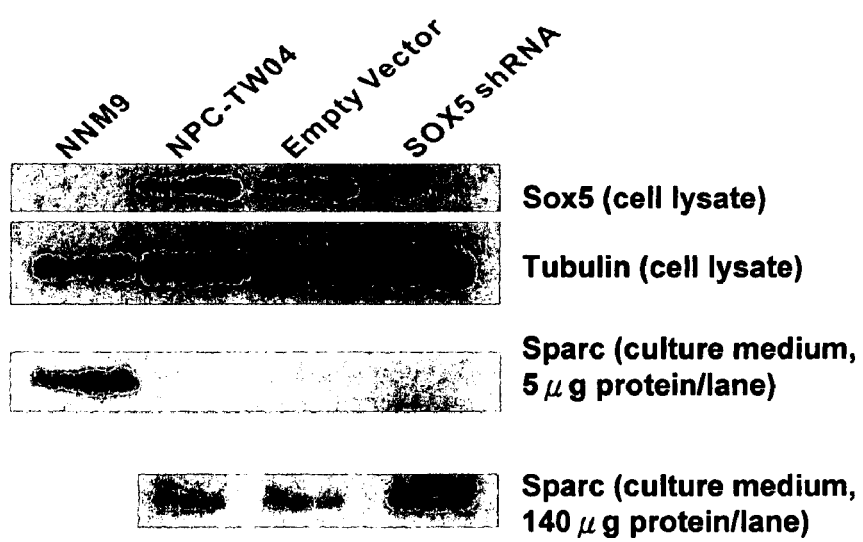

FIG. 2 shows the expression of FGFR1 and SPARC genes after knocking-down SOX5 in NPC cells. A, comparison of mRNA copy numbers in SOX5 shRNA or empty vector transfected NPC cells determined by Q-RT-PCR; a: SOX5, b: FGFR1, c: SPARC. Y-axis: relative mRNA copy numbers. B, Sox5 and Sparc protein levels in normal nasomucosal cells, NPC cells, SOX5 shRNA or empty vector transfected NPC cells detected with Western blot analysis.

Figure 3:
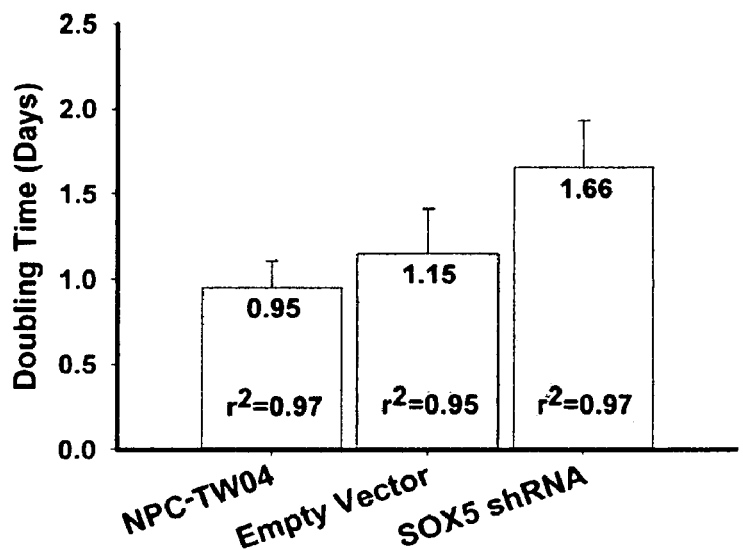
Figure 3:
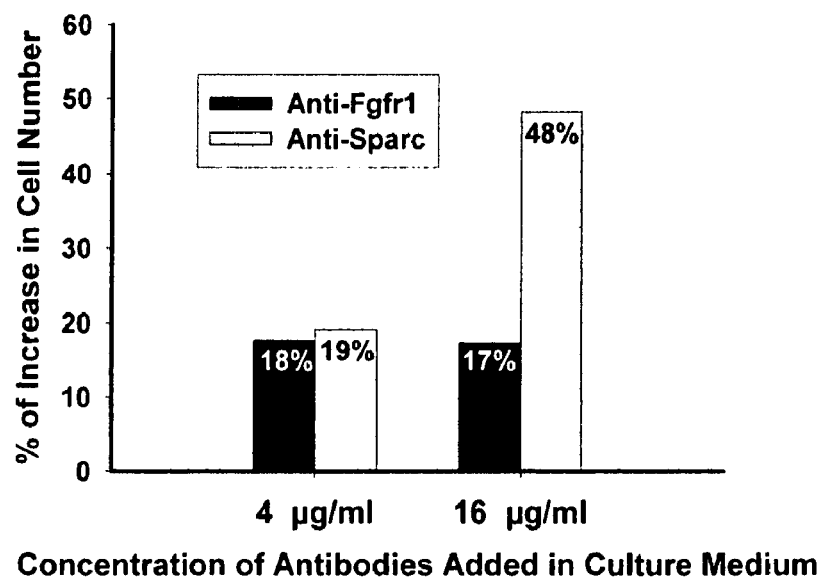

FIG. 3 shows the effects of knocking-down SOX5 on NPC cell division. A, doubling time for NPC cells, SOX5 shRNA or empty vector transfected NPC cells detected with MTT analysis. Y-axis: doubling time (day). B, cell proliferation rate (%) after knocking-down SOX5 in NPC cells, detected with MTT analysis after adding anti-Fgfr1 or anti-Sparc antibodies respectively. X-axis: concentration of antibodies added; Y-axis: cell proliferation rate (%).

Figure 4:
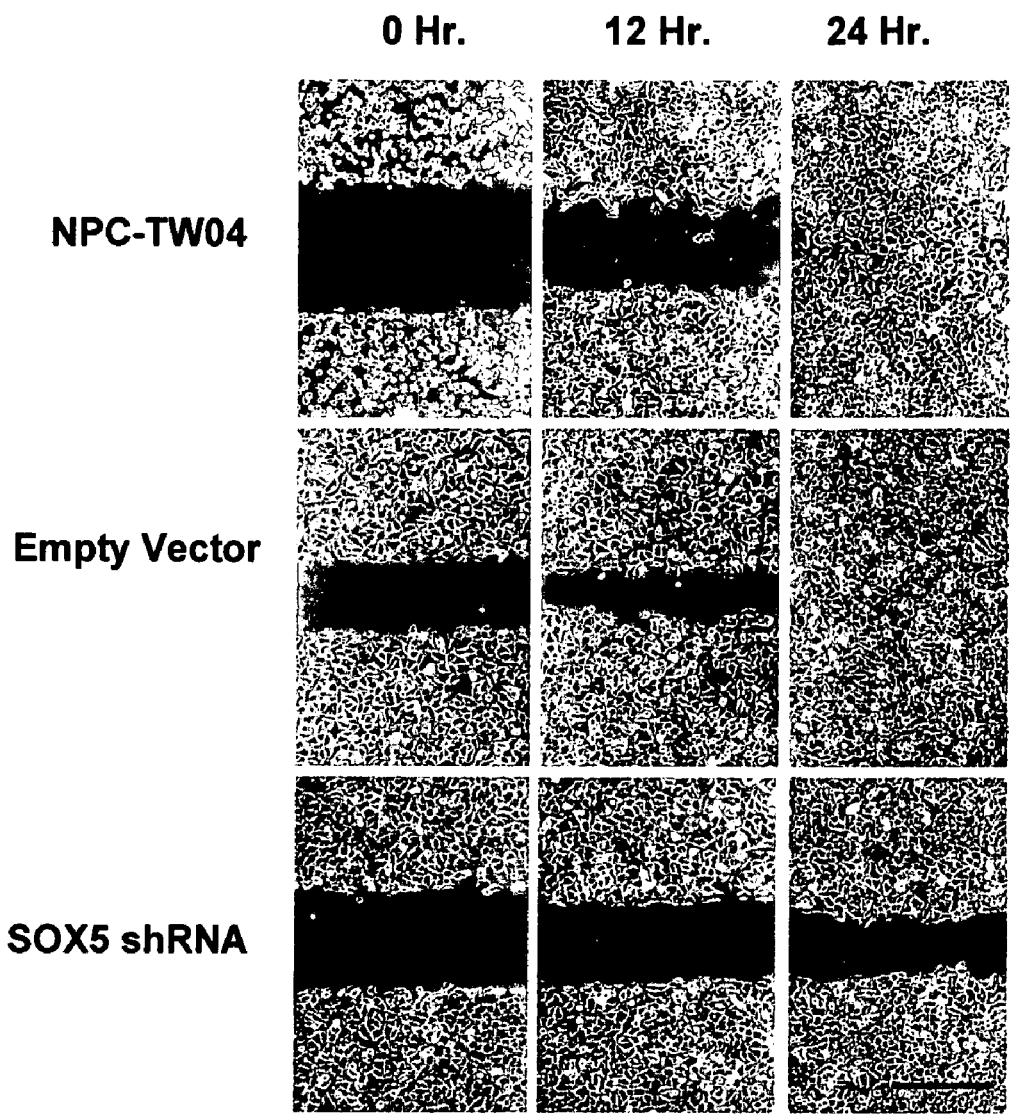

FIG. 4 shows the cell migration of NPC cells, SOX5 shRNA or empty vector transfected NPC cells at 0, 12 and 24 h of the scratch migration assay.

Figure 5:
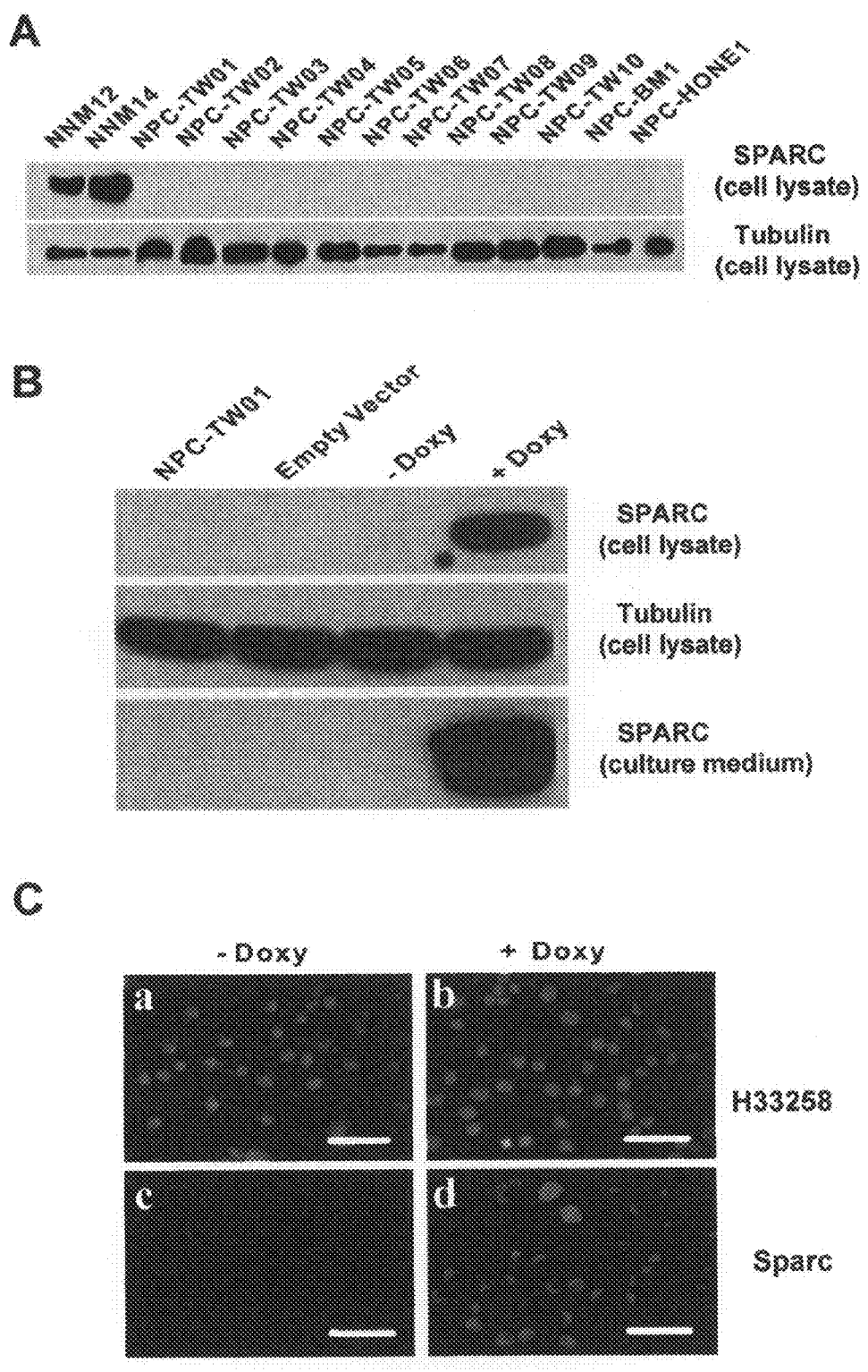

FIG. 5 shows Sparc protein expression in normal nasomucosal cells, NPC cells, and pBIG2i-SPARC transfected NPC cells. A, Sparc proteins in cell lysates of normal nasomucosal cell lines and NPC cell lines detected with Western blot analysis using tubulin as the internal control B, Sparc protein in cell lysates and cell culture media of NPC cells, pBIG2i-SPARC transfected NPC cells with or without doxycycline addition using tubulin as the internal standard. C, immunohistochemical staining of Sparc protein in NPC cells.

Figure 6:
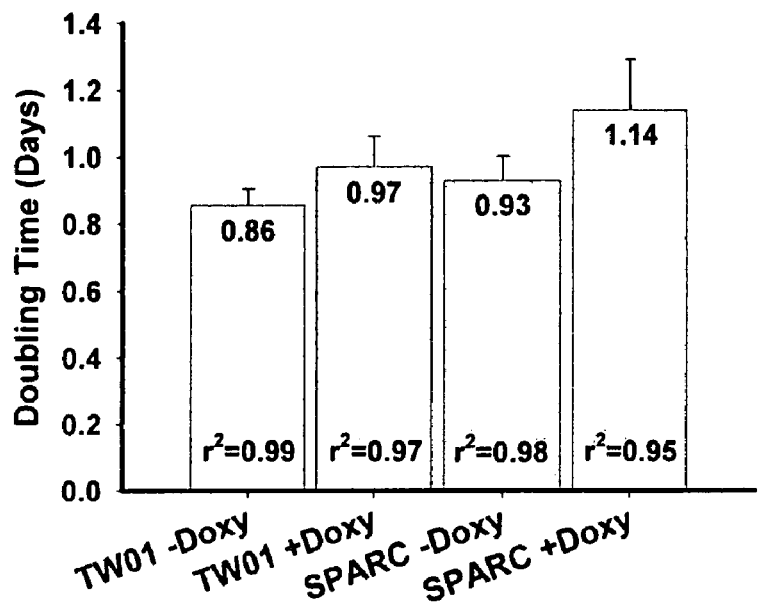
Figure 6:
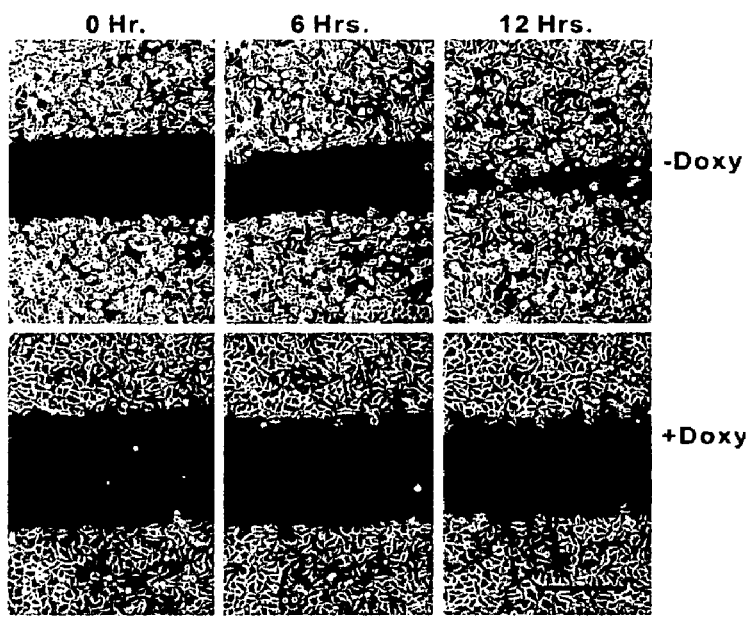

FIG. 6 shows the effects on cell proliferation and migration of SPARC overexpression induced by doxycycline. A, Doubling times determined with MTT assay from cells transfected with pBIG2i plasmid containing SPARC gene or NPC cells containing no inserted gene (empty vector) in the presence or in the absence of doxycycline. B, the cell growth of pBIG2-SPARC plasmid transfected NPC cells at 0, 6 and 12 h of the scratch migration assay in the presence or in the absence of doxycycline.

Figure 7:
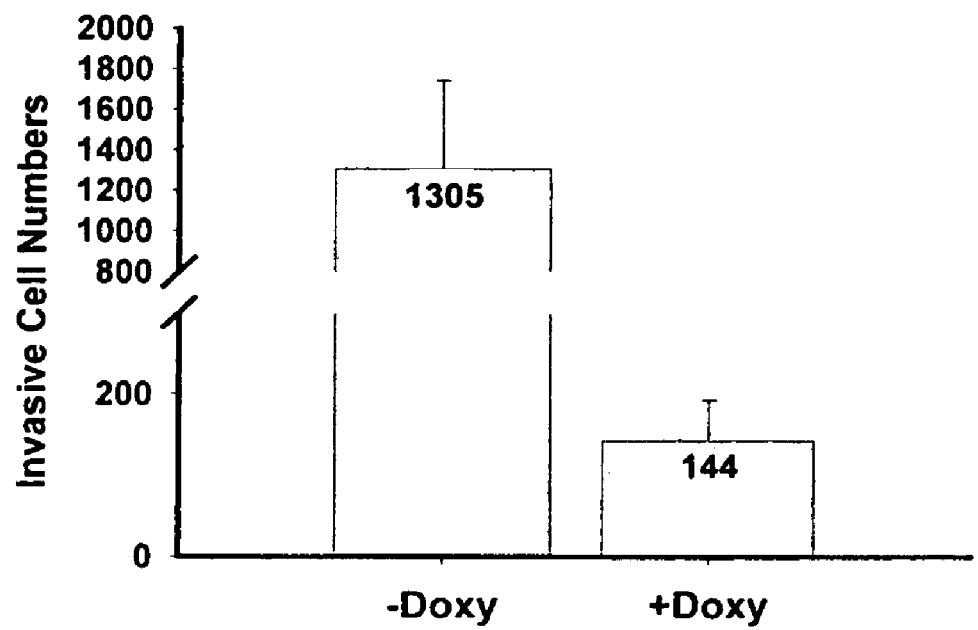

FIG. 7 shows the effects of SPARC overexpression on NPC cell line's invasion activity using the membrane invasion chamber system in the presence or in the absence of doxycycline.

Figure 8:
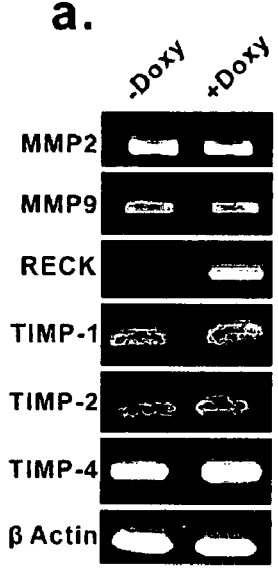
Figure 8:
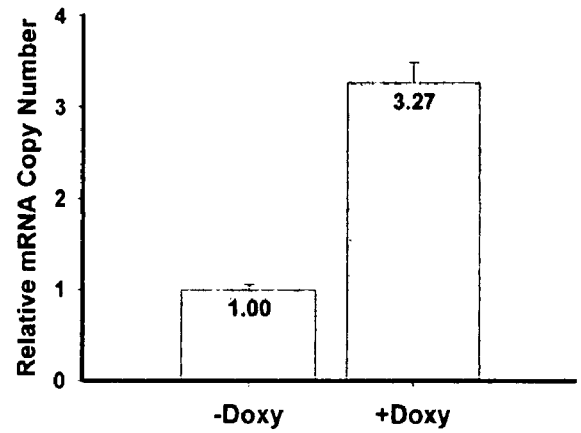
Figure 8:
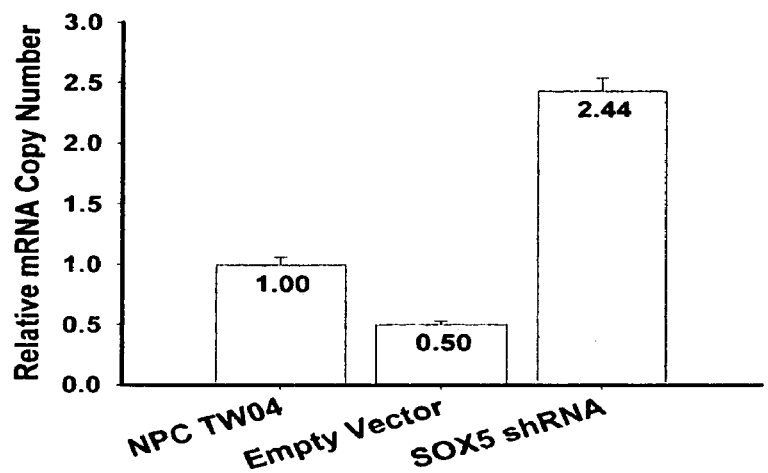

FIG. 8 shows the effects of SOX5 knocking-down and SPARC overexpression on RECK gene. A-a, mRNA expression of MMP2, MMP9, RECK, TIMP-1, TIMP-2 and TIMP-4 determined with semi-quantitative RT-PC in pBIG2i-SPARC plasmid transfected NPC cells in the absence or presence of doxycycline, β-actin was served as the internal control. A-b, the mRNA copy numbers of RECK determined with Q-RT-PCR under the control of doxycycline. B, the mRNA copy numbers of RECK determined with Q-RT-PCR on NPC cells, SOX5 shRNA and empty vector transfected NPC cells.

Figure 9:
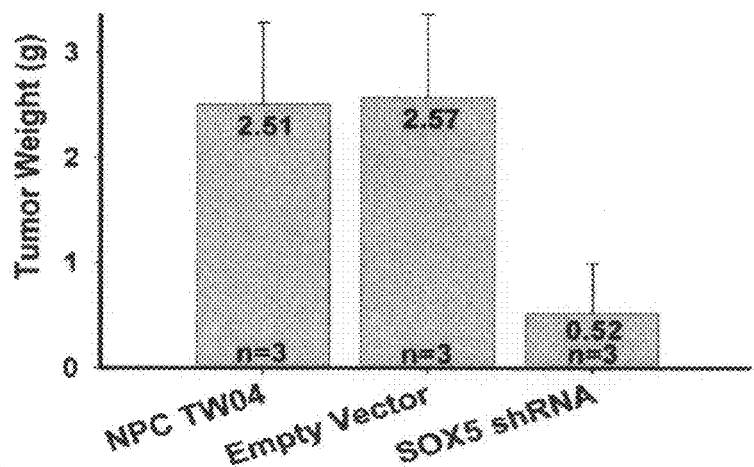
Figure 9:
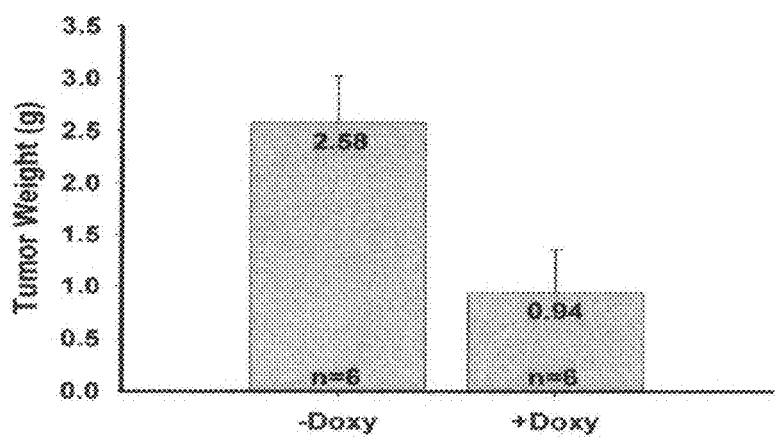
Figure 9:
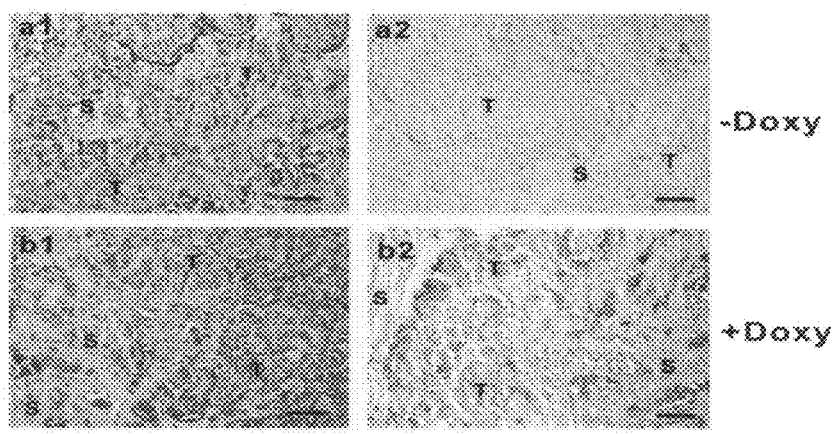

FIG. 9 shows the in vivo experiments of SOX5 knocking down and SPARC overexpression. A, the weights of NPC xenograft tumor in the NOD SCID mice injected with NPC-TW04 cells, NPC-TW04 cells transfected with pSM2C plasmid containing SOX5 shRNA or empty plasmid. B, the weights of NPC xenograft tumor in the NOD SCID mice injected with pBIG2i-SPARC transfected NPC cells in the presence or absence of doxycycline. C, the morphology and immunostaining of SPARC protein in xenograft tumor sections from B; a1: H&E staining in the absence of doxycycline, a2: immunostaining of SPARC protein in the absence of doxycycline, b1: H&E staining in the presence of doxycycline, b2: immunostaining of SPARC protein in the presence of doxycycline.

Figure 10:
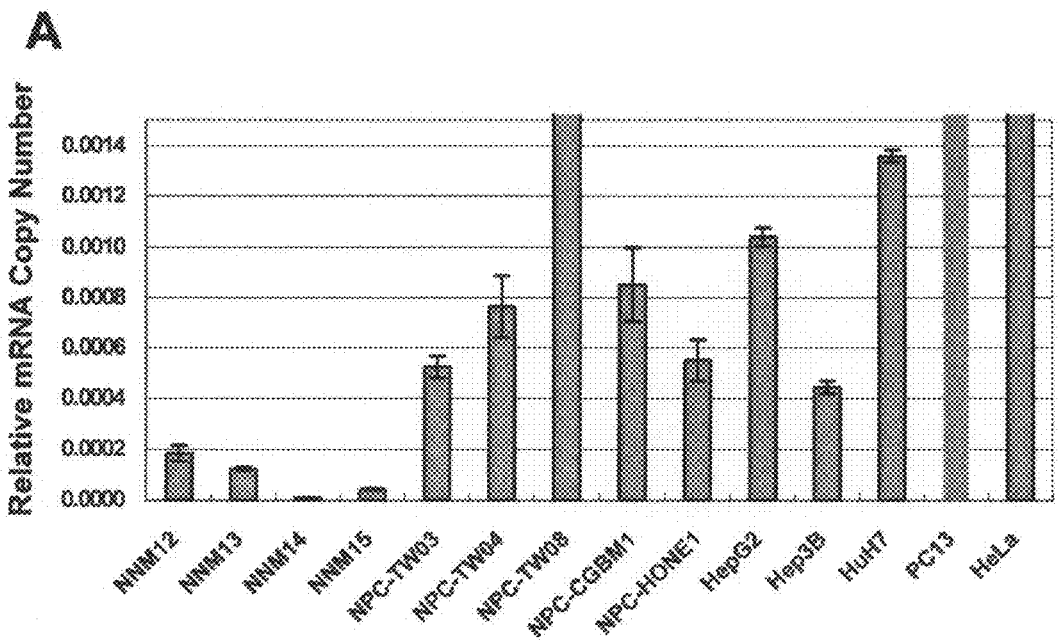
Figure 10:
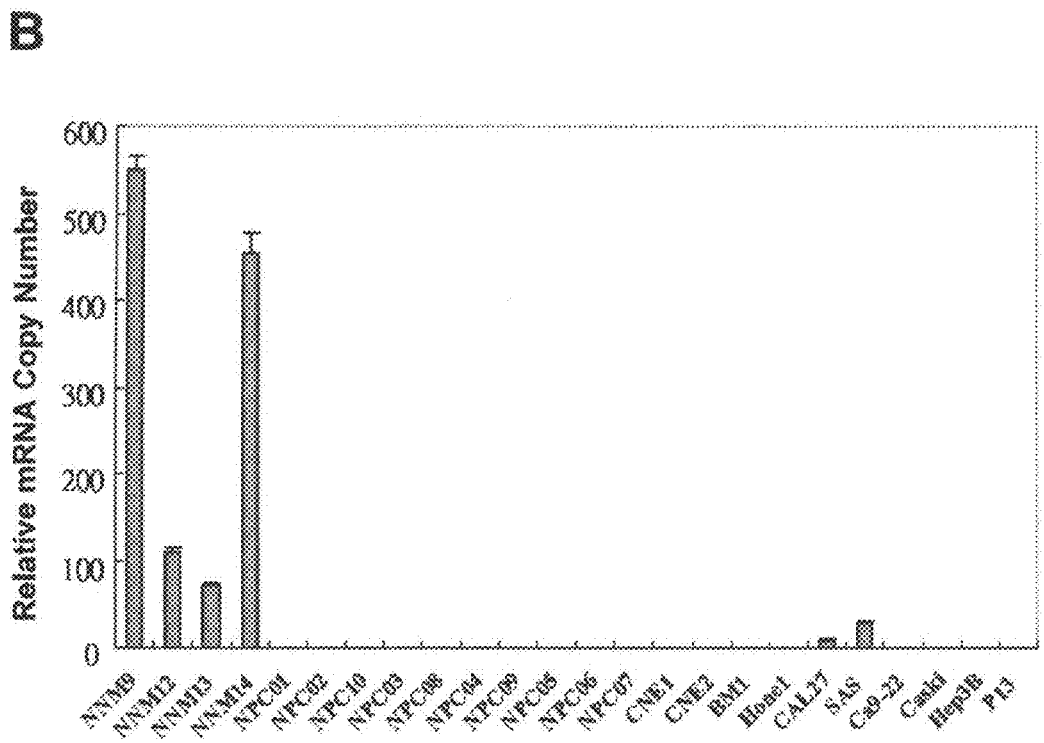

FIG. 10A shows Q-RT-PCR analysis of the SOX5 expression in normal nasomucosal cells and other cancer cells. FIG. 10B shows Q-RT-PCR analysis of the SPARC expression in normal nasomucosal cells and different cancer cell lines.

Figure 11:
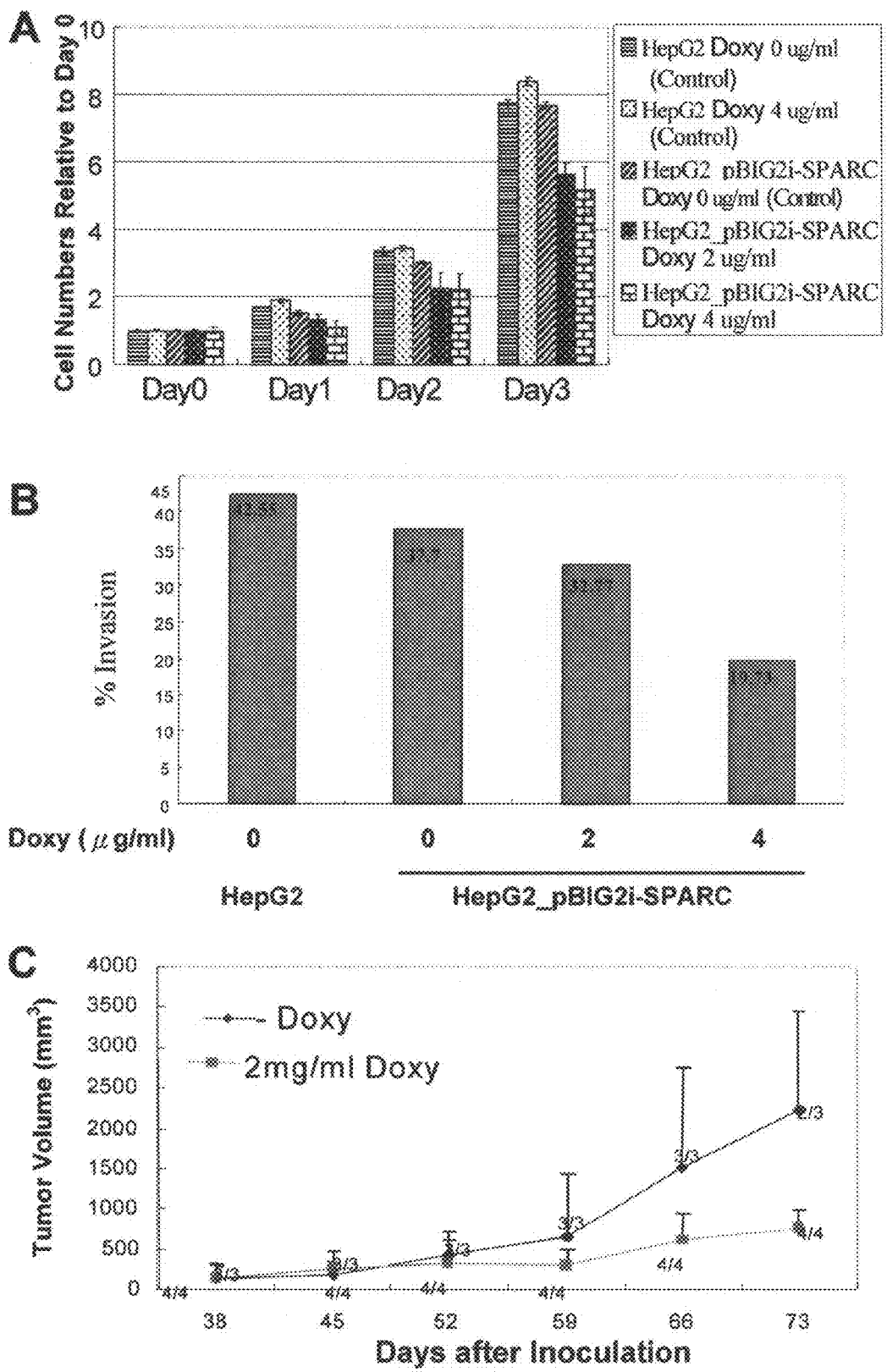

FIG. 11 shows the biological functions of SPARC overexpression induced by doxycycline in liver cancer cells. A, MTT assay determined cell proliferation rates of HepG2 cells and pBIG2i-SPARC transfected HepG2 cells in the presence or absence of doxycycline. B, the invasion activities determined with the membrane invasion chamber system of HepG2 cells and pBIG2i-SPARC transfected HepG2 cells in the presence or absence of doxycycline. C, Sizes of xenograft tumors in NOD SCID mice injected with pBIG2i-SPARC transfected liver cancer cells in the presence or absence of doxycycline.

DETAILED DESCRIPTION OF THE PREFERRED EMBODIMENT

The present invention discloses effective indices for cancer diagnosis using the expression levels of SOX5 and/or SPARC, wherein the cancer is nasopharyngeal cancer, liver cancer, lung cancer, or uterine cervical cancer. The expression levels of SOX5 and/or SPARC are effective indicators since expression of genetic marker SOX5 was increased, and the expression of SPARC was decreased in cancer patients with distant metastasis and poor prognosis. The expression levels of SOX5 and/or SPARC can be used in determining a cancer patient for the development of distant metastasis or poor prognosis of a cancer, and the SOX5 and/or SPARC genes can provide important information for targeting treatment of the cancer.

The present invention provides a method for predicting a cancer patient for the development of distant metastasis or poor prognosis of a cancer since the changes of SOX5 and/or SPARC expression levels are closely related to distant metastasis or poor prognosis of cancer, wherein the cancer is nasopharyngeal cancer, liver cancer, lung cancer, or uterine cervical cancer. The method comprises: obtaining a sample from a cancer patient; evaluating the expression levels of SOX5 and/or SPARC; comparing with the expression levels of SOX5 and/or SPARC from a normal non-cancer tissue; judging the risk for the development of distant metastasis or poor prognosis of cancers by the increase or decrease in expression levels of genetic markers. There is a high risk for the development of distant metastasis or poor prognosis of cancers if the expression level of SOX5 is higher than that of non-cancer sample or the expression levels of SPARC is lower than that of non-cancer sample.

The abovementioned expression levels of the genetic markers SOX5 and/or SPARC can be shown in mRNA levels. The changes of mRNA levels of SOX5 and/or SPARC in cancer biopsy specimens or non-cancer biopsy specimens can be easily determined with any relevant analysis techniques, which include but are not limited to Northern blotting, Reverse Transcription Polymerase Chain Reaction (RT-PCR), real time quantitative PCR (Q-RT-PCR) and the like, by the person skilled in the art after reading the patent disclosure information.

Specifically, the method includes evaluating the mRNA levels of the genetic markers SOX5 and/or SPARC in the biopsy samples, then comparing the mRNA levels of the genetic markers SOX5 and/or SPARC from cancer samples with those from non-cancer samples.

In addition, the gene expression levels of SOX5 and/or SPARC can be shown in protein levels. The changes of protein levels of SOX5 and/or SPARC in cancer biopsy specimens or non-cancer biopsy specimens can be easily determined with the relevant protein analysis techniques, which include but are not limited to enzyme linked immunosorbent assays (ELISA), immunofluorescence, immunohistochemistry, enzyme immunoassay (EIA), radioimmunoassay, Western blotting and so on, by the person skilled in the art after reading the patent disclosure information.

Specifically, another method includes evaluating the protein levels of the genetic markers SOX5 and/or SPARC in the biopsy samples, then comparing the protein levels of the genetic markers SOX5 and/or SPARC from cancer samples with those from non-cancer samples.

Screening of drugs in cancer therapy can be performed through determining the expression levels of genetic markers SOX5 and/or SPARC. The cancer in particular is nasopharyngeal cancer, liver cancer, lung cancer, or uterine cervical cancer. For example, the promoter region of genetic markers SOX5 and/or SPARC can be linked to a green fluorescent protein gene as a reporter for monitoring fluorescent intensity of testing drug treated cells. The details of the examples are described as follows:

Example 1

Comparison on Gene Expression Profile Changes of NPC Cells and Normal Nasomucosal Cells Analysis of gene expression profiles from NPC cells or normal nasomucosal cells (NNM) using Microarray was carried out to identify the up-regulated and down-regulated gene sets. Primary cultures of normal nasomucosal cells NNM6, NNM9, NNM11 and NNM14 were obtained from 4 patients with nasal polyps undergoing polypectomy in National Taiwan University Hospital. After surgical removal, the nasal polyps specimens were immersed immediately in DMEM containing 10% fetal bovine serum (FBS) and maintained at 4° C. The tissue parts were cut, transferred to a Petri dish and cultivated in serum-free DMEM medium containing growth factors of insulin, transferin, selenium, bovine serum albumin, linoeic acid, hydrocortisone (1.25 μg/ml), cholera toxin (0.3 μg/ml), bovine pituitary extract (70 μg/ml), epidermal growth factor (25 μg/ml), endothelial cell growth supplement (0.1 μ/ml), 5-methyl-2'-deoxycytidine (0.0386 mg/ml), nutri-doma-SP (Boehringer Mannheim). When the NNM cell culture reached the $6^{th}$ generation, the medium was replaced with DMEM containing 20% FBS and cultivated to the $19^{th}$ or $20^{th}$ generation. NPC cell lines comprise 10 cell lines of NPC-TW01~NPC-TW10, NPC-BM1, a nasopharyngeal carcinoma cell line derived from a bone marrow metastatic lesion provided by Dr. S. K. Liao, and NPC-HONE1, established in China. These 12 cell lines, NPC-TW01~NPC-TW10, NPC-BM1 and NPC-HONE1, were cultivated at 37° C. with 5% $CO_2$ in DMEM containing 5% FBS. These cell lines can be cultivated more than $100^{th}$ passages.

Total RNA was extracted from cancer cells using Nucleo Spin total RNA extraction kit (Macherey-Nagel Inc.) and quantified with an agarose gel. cDNA was synthesized with SuperScript II RT kit (Invitrogen). Twenty nine genes showed significant differences between NPC and normal nasomucosal cells after analysis of gene expression profile using a cDNA microarray. These 29 genes are: ATF2, CDK2AP1, CENPF, CITED2, COROIC, EIF3S4, ELJ20642, FZD1, GCA, IGFBP6, IGTAE, KLF7, MEF2C, NAB2, P4HA2, PEC1, PLOD, ROD1, Cox-2, EIF5A, FGFR1, KIAA0611, RPL37, ITGA5, OPG, PTPD1, SPARC, TSP-1, and UCHL1.

The gene expression levels of the 29 genes were confirmed with Q-RT-PCR. Total RNA was extracted from cancer cells as described. cDNA was synthesized with 1 μg of total RNA with oligo-dT as primers. PCR reactions contained 4 μl of the 200-fold diluted cDNA, 5 μl of SYBER Green PCR Master Mix (PE Biosystems. Foster City, Calif., USA), 0.5 μl of 6M forward primer and 0.5 μl of 6M reverse primer were performed in an ABI PRISM 7700 Sequence Detection System (Applied Biosystems) for the direct quantification of transcription products. Samples were heated at 50° C. for 2 min, followed by 95° C. for 10 min, then subjected to 40 cycles of 95° C. for 15 sec and 60° C. for 1 min, and terminated at 95° C. for 15 sec, 60° C. for 20 sec, and 95° C. for 15 sec. Forward and reverse primers were designed by Primer Express software (Applied Biosystems). The mRNA expression of house keeping gene, glyceraldehyde-3-phosphate dehydrogenase (GAPDH), was served as an internal reference. The results were calibrated with house keeping genes to adjust the variances among samples. The specificity of the PCR products was assessed by the melting curve analysis to check for the presence of nonspecific products and primer dimmers. Statistical analysis was performed using Student's t-test. Statistical significance was set at $p<0.05$.

Samples used for first round of Q-RT-PCR were 2 normal nasomucosal cell lines (NNM4 and NNM6), and 6 NPC cell lines (NPC-TW01~TW06). Six genes were identified to be down-regulated (significantly inhibited): FGFR1, IGFBP6, KLF7, RPL37, SPARC and UCHL1 (Table 1).

TABLE 1

Results of first round of Q-RT-PCR

| gene | Normal nasomucosal cells from 2 cell lines | | NPC cells from 6 cell lines | | |
|---|---|---|---|---|---|
| | copy No. of mRNA | Standard deviation | copy No. of mRNA | Standard deviation | P-value |
| ATF2 | 0.0670621160 | 0.0337503620 | 0.0788799050 | 0.0686119030 | 0.8289 |
| CDK2AP1 | 17.9308759300 | 8.5206460750 | 15.5325192700 | 11.0537955700 | 0.7924 |
| CENPF | 0.0154168970 | 0.0121599750 | 0.8404781250 | 1.6020302720 | 0.5154 |
| CITED2 | 2.2721504930 | 1.6877010550 | 0.7498703720 | 0.5827377440 | 0.076 |
| CORO1C | 1.8622455300 | 0.6156791970 | 16.5401738400 | 33.5512659400 | 0.5787 |
| Cox-2 | 0.0000005617 | 0.0000002325 | 2.0309022330 | 4.6395641120 | 0.5784 |
| EIF3S4 | 0.0002915840 | 0.0004107990 | 0.0164232010 | 0.0246305420 | 0.4134 |

TABLE 1-continued

Results of first round of Q-RT-PCR

| gene | Normal nasomucosal cells from 2 cell lines | | NPC cells from 6 cell lines | | |
|---|---|---|---|---|---|
| | copy No. of mRNA | Standard deviation | copy No. of mRNA | Standard deviation | P-value |
| eIF5A | 34.0173612100 | 41.0135057900 | 67.4683788900 | 72.4955361900 | 0.5704 |
| FGFR1 | 4.2370415310 | 0.8984154960 | 0.0327979750 | 0.0295249130 | 0.0001 |
| FLJ20642 | 0.0002654050 | 0.0003737750 | 0.0005741520 | 0.0012818820 | 0.7595 |
| FZD1 | 1.3918311520 | 0.8960364130 | 0.5354936980 | 0.7385817960 | 0.2205 |
| GCA | 0.0461157870 | 0.0496444510 | 0.1143312030 | 0.1637404520 | 0.5997 |
| IGFBP6 | 15.1234905500 | 4.7485417330 | 3.6085917160 | 3.7337841170 | 0.0114 |
| IGTAE | 0.0000005617 | 0.0000002325 | 0.0000197161 | 0.0000471182 | 0.6052 |
| Integrin 5 alpha | 19.4085567000 | 25.7047431400 | 175.9321761000 | 295.0987865000 | 0.5037 |
| KIAA0611 | 0.0000005617 | 0.0000002325 | 0.0885227810 | 0.0829738630 | 0.2023 |
| KLF7 | 0.4374653480 | 0.0575614880 | 0.1448557040 | 0.1099614670 | 0.0132 |
| MEF2C | 17.6669691300 | 24.8681921000 | 0.0575575700 | 0.1192640450 | 0.0778 |
| NAB2 | 0.0000018045 | 0.0000007805 | 1.8319917360 | 1.4348451850 | 0.1376 |
| OPG | 416.6550143000 | 588.5843652000 | 0.0000481661 | 0.0001153290 | 0.0779 |
| P4HA2 | 2.7594028510 | 0.5831842050 | 4.0079476090 | 3.1926628000 | 0.6198 |
| PECI | 9.5159069030 | 0.2451524580 | 4.9190092470 | 4.5022549410 | 0.2199 |
| PLOD | 24.9396082600 | 35.2699289100 | 2.5207549190 | 1.3325791710 | 0.1061 |
| PTPD1 | 2.0935376550 | 2.5892427030 | 0.3301621140 | 0.3254181550 | 0.0968 |
| ROD1 | 6.9918346210 | 8.9230395700 | 26.4169653000 | 59.3806025400 | 0.6768 |
| RPL37 | 4981.7455950000 | 1931.4052070000 | 615.5103187000 | 858.7542617000 | 0.003 |
| SPARC | 328.9748257000 | 311.1045242000 | 0.0074010530 | 0.0119851850 | 0.0193 |
| TSP-1 | 234.5018176000 | 329.1176923000 | 1.0997575010 | 1.1089576820 | 0.0775 |
| UCHL1 | 23.4488206500 | 1.9285766820 | 0.0000015054 | 0.0000032014 | <0.0001 |

Next, second round of Q-RT-PCR was carried out with the abovementioned 6 genes and samples from 5 normal nasomucosal cell lines (NNM4, NNM6, NNM9, NNM11 and NNM14), and 7 NPC cell lines (NPC-TW01~TW07). Only two genes were identified to be down-regulated (significantly inhibited) from this experiment: FGFR1 and SPARC (Table 2).

TABLE 2

Results of second round of Q-RT-PCR

| gene | Normal nasomucosal cells from 2 cell lines | | NPC cells from 6 cell lines | | |
|---|---|---|---|---|---|
| | copy No. of mRNA | Standard deviation | copy No. of mRNA | Standard deviation | P-value |
| FGFR1 | 3.7430601786 | 4.2016460306 | 0.0308268587 | 0.0274523380 | 0.0382 |
| IGFBP6 | 12.0880771712 | 12.8159949804 | 3.2134864773 | 3.5651615550 | 0.1072 |
| KLF7 | 1.3475750188 | 2.5239999859 | 0.1510488690 | 0.1017091800 | 0.2299 |
| RPL37 | 2037.9850053302 | 2856.9958887137 | 555.1044587743 | 800.0569628000 | 0.2144 |
| SPARC | 222.3496794676 | 260.4493977811 | 0.0500125081 | 0.1132689570 | 0.0439 |
| UCHL1 | 36.1480105236 | 55.8372479047 | 0.0047651548 | 0.0126034320 | 0.1111 |

The results from cDNA microarray and real-time PCR showed that FGFR1 and SPARC genes in NPC cells were significantly inhibited.

Example 2

Correlation Between SOX5 Expression Level and Distant Metastasis/Prognosis

FGRF1 is a fibroblast growth factor receptor, while SPARC is a secreted protein acidic and rich in cysteine, which is a matricellular protein. The functions of both proteins showed no significant correlation. However, both genes were significantly inhibited in the abovementioned example 1. The study of the invention was to confirm whether both genes shared the same transcription factor/factors, or were regulated by the transcription factor/factors.

Transcriptional start sites (promoter regions) for both FGFR1 and SPARC gene sequences were searched using the Database of Transcriptional Start Sites, DBTSS, a public resource for the analysis of promoter regions. The bioinformatics information obtained was used to search for the transcription factors binding to both genes from the TRANSFAC database. Transcription factors Sox5, Nrf1 and tinman were found to be shared by both the FGFR1 and SPARC genes. Therefore, the expressional levels of these 3 transcription factors Sox5, Nrf1 and tinman between NPC cells and nasomucosal cells were compared. mRNA levels were compared using Q-RT-PCR as described in Example 1. The mRNA levels of NRF1 and tinman showed no significant difference between NPC cells and nasomucosal cells, only mRNA level of SOX5 gene was significantly higher in NPC cell lines than that in normal nasomucosal cells (Table 3). SOX 5 gene may regulate the tumor suppressor gene of NPC.

TABLE 3

Q-RT-PCR Results of SOX5, Nrf1 and tinman genes

| gene | Normal nasomucosal cells from 2 cell lines | | NPC cells from 6 cell lines | | |
|---|---|---|---|---|---|
| | copy No. of mRNA | Standard deviation | copy No. of mRNA | Standard deviation | P-value |
| Nkx2.5 (tinman) | 0.000239289 | 0.000272595 | 0.000519493 | 0.000322313 | 0.1458 |
| Nrf1 | 0.003878201 | 0.001733216 | 0.009878979 | 0.006249378 | 0.0659 |
| SOX5 | 0.000185655 | 0.000161995 | 0.000540935 | 0.00020177 | 0.0088 |

Figure 1:
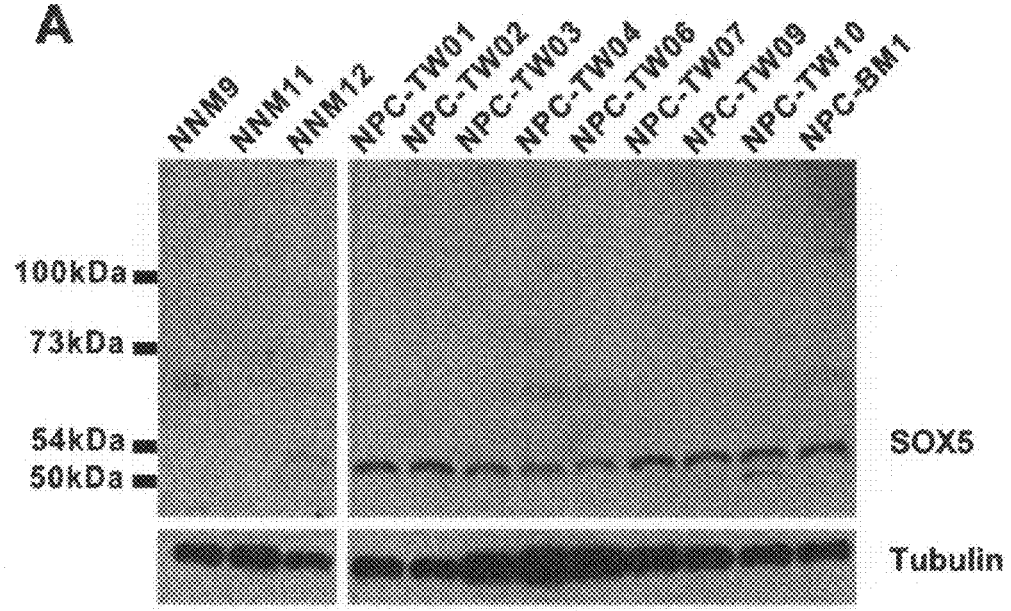
FIG. 1 shows the Sox5 protein expression in NPC cells. A, the expression of Sox5 in normal nasomucosal cells (NNM)
Figure 1:
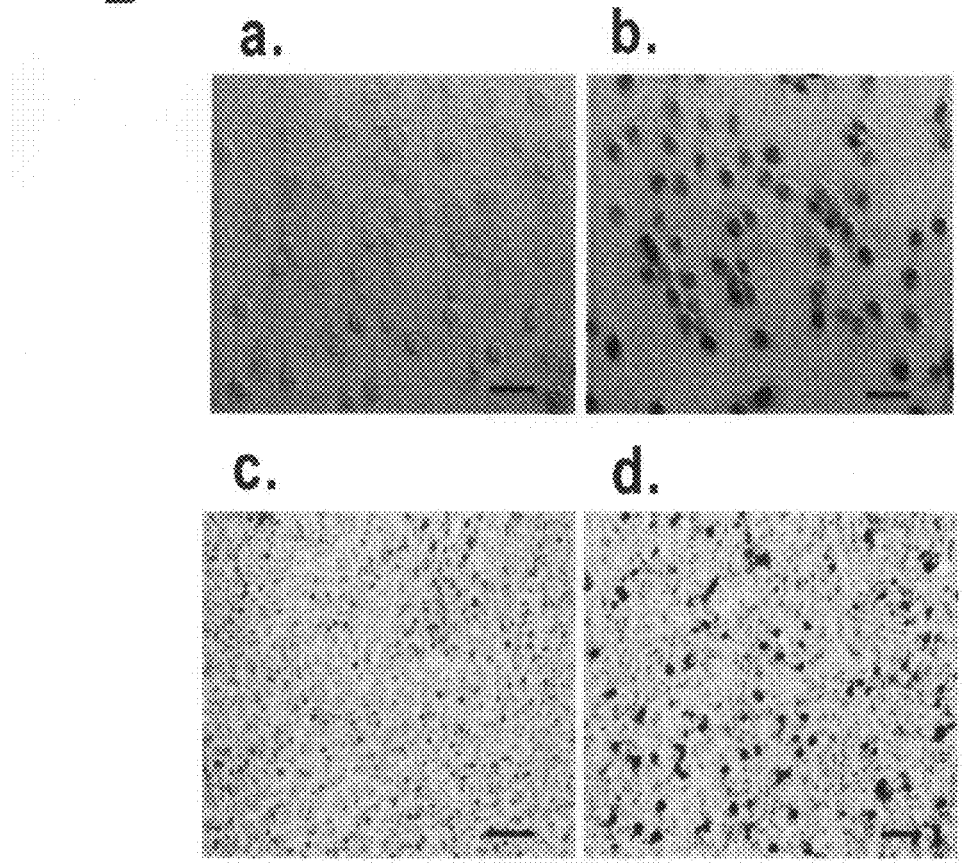

Western blotting was performed to compare the Sox5 protein levels between NPC cells and nasomucosal cells to confirm the correlation between NPC and SOX5 gene. Total cell lysates from NPC cells and nasomucosal cells were collected from $1 \times 10^6$ cells. The protein concentrations were determined with UV280. Proteins were separated by polyacrylamide gel electrophoresis at 30 mA for 1 h, and transferred to polyvinylidene difluoride (PVDF) membranes. Immunoblotting was performed using primary antibody of chicken anti-Sox5 antibody at room temperature for 1 h, followed by secondary antibody HRP conjugated goat anti-chicken IgY antibody at room temperature for 1 h, and detected with enhanced chemiluminescence (ECL) reagent. FIG. 1A showed that NPC cells NPC-TW01, NPC-TW02, NPC-TW03, NPC-TW04, NPC-TW06, NPC-TW07, NPC-TW09, NPC-TW10 and NPC-BM1 had high levels of Sox5 protein, while normal nasomucosal cells NNM9, NNM11 and NNM12 had little or no Sox5 protein using tubulin, a house keeping protein, as the internal control. Therefore, Sox5 protein was more abundant in NPC cells than in normal nasomucosal cells.

Both Western blotting and Q-RT-PCR analysis showed that SOX5 gene is highly expressed in NPC cells. The expression of SOX5 gene in NPC cell lines and biopsy specimens were also analyzed with immunohistochemistry staining. Culture cells were fixed on cover glasses, incubated with a chicken anti-Sox5 antibody (Asia Hepto Genes Co.) at room temperature for 12 h, followed by biotin-labeled secondary antibody anti-chicken IgY at room temperature for 1 h. The unreacted antibodies were removed with buffer. The avidin-biotin-peroxidase complex method (Avidin-Biotin Peroxidase Complex immunostaining kit, ABC immunostaining kit, Victor) was used for the immunohistochemistry staining. FIG. 1B-*a* showed the result as negative control using normal chicken blood IgY antibody to replace Sox5 antibody, the rest steps were the same as abovementioned. However, a fraction of NPC cells revealed strong reaction product anti-Sox5 in the culture cells (FIG. 1B-*b*). This step confirmed that the reaction products were interacted with Sox5 antibody. The biopsy of 28 NPC patients was obtained from Department of Pathology in National Taiwan University Hospital. Two of the cancer patients survived more than 5 years and had no recurrence of NPC showed almost no Sox5 positive cells in their biopsy specimens (FIG. 1B-*c*). It appeared that the Sox5 protein levels were quite low or even no expression in the early stage of local NPC. Eight of the NPC patients had distant metastatsis to liver, lung, bone marrow, cerebrum, or spinal cord showed many Sox5 positive stained cells in biopsy specimens (FIG. 1B-*d*). Seventeen patients with head metastatsis showed intermediate number of Sox5 positive stained cells in biopsy specimens (data not shown). The results shown in above reveal obvious Sox5 protein expression in biopsy specimens when NPC patients have poor prognosis or distant metastatsis, while weak or no Sox5 protein is detected in patients with early stage of local NPC. Collectively, the expression levels of SOX5 gene can be a genetic marker for predicting the development of distant metastasis and poor prognosis of cancers.

Example 3

The Effects of SOX5 Knocking-Down on NPC Cells

RNA interference (RNAi)-mediated knocking-down of transcription factor SOX5 gene was performed to determine if Sox5 could down-regulate FGFR1 and SPARC genes. The expression of both FGFR1 and SPARC genes were monitored after SOX5 gene was knocked down. Gene silencing by RNA interference inducing degradation of specific RNA using small interfering RNAs (siRNAs) or short hairpin RNAs (shRNAs) has become a valuable genetic tool. The SOX5 shRNA was cloned into a pSM2C vector. This SOX5 shRNA containing plasmid was transfected into NPC-TW04 cells with transfection AI reagents. A pSM2C vector containing no SOX5 shRNA or an unrelated shRNA served as a control. Q-RT-PCR analysis on the pSM2C-SOX5-shRNA vectors transfected NPC-TW04 cells showed that the SOX5 gene was knocked-down by SOX5 shRNA. The mRNA of SOX5 was inhibited by SOX5 shRNA in comparison with the un-transfected NPC-TW04 cells (FIG. 2A-*a*). This model can be applied in studies of Sox5 effect on regulation of downstream genes FGFR1 and SPARC. The mRNA of FGFR1 and SPARC increased after SOX5 was knocked-down according to the assessment of Q-RT-PCR analysis (FIG. 2A-*b*, 2A-*c*). The mRNA level of FGFR1 increased around 2.3 folds while the mRNA level of SPARC increased up to 106.66 folds. The culture media was concentrated to 80-100 folds after ultrafiltration using a membrane filter with molecular weight cut-off 10 kDa MW (Amicon Ultra-4, Millipore, USA) by centrifugation at 500 g for 8 h at 4° C. The protein levels of Fgfr1 and Sparc in the culture media were determined with Western blotting using primary antibody of mouse anti-Fgfr1 antibody and mouse anti-Sparc antibody respectively, and secondary antibody goat anti-mouse IgG antibody as described in Example 1. The Fgfr1 protein was not detected though the mRNA levels of FGFR1 increased (data not shown). The Sparc protein was increased and secreted into the culture media when the mRNA level of SPARC increased more than 100 folds (FIG. 2B). In summary, inhibition of the SOX5 gene in NPC cells will cause increase in the expression of downstream genes FGFR1 and SPARC. That is, the FGFR1 and SPARC genes were inhibited by the SOX5 gene in NPC cells, especially the SPARC gene. This is the first proof for inhibition of the downstream SPARC gene by the SOX5 gene in NPC cell.

The roles of SOX5 gene in NPC cell functions such as doubling time and migration were studied by transfection of SOX5 shRNA containing plasmid. MTT assay is commonly used to analyze cell proliferation. MTT (3[4,5-dimethylthiazol-2-yl]-2,5-diphenyltetrazolium bromide) is a yellow dye which can be converted to water-insoluble purple formazan on the reductive cleavage of its tetrazolium ring by the succinate tetrazolium reductase in mitochondria of cells. The amount of formazan produced is used to detect the number of viable cells and calculate the survival rates. Cells were seeded onto 96-well plates at 2000 cells per well. After cultivated for 0, 2, 3, 4 days, DMEM containing 5% FBS and 100 µl, 2 mg/ml of MTT were supplemented to each well and incubated at 37° C. for 4 h The generated dark crystals formazan were dissolved by 150 µl of DMSO. The absorbances were measured at 540 nm with 100 µl of solution in an ELISA Reader and compared with the standard curve of cell numbers to calculate the doubling time. The results are shown in FIG. 3A. The doubling time of SOX5 shRNA transfected NPC cells NPC-TW04, compared to that of the un-transfected NPC cells or NPC cells transfected with pSM2C plasmid containing no insert, were prolonged to at least 12 h. This revealed that the inhibition of SOX5 would hinder the division of NPC cells, further to delay the doubling time of NPC cells.

The cell migration ability of SOX5 shRNA transfected NPC cells (NPC-TW04) was examined using a scratch migration assay. The basic steps involve creating a 2-3 mm "scratch" in a cell monolayer with a pipette tip, capturing the images at the beginning and every 6 h. The un-transfected NPC cells or NPC cells transfected with pSM2C plasmid containing no insert were served as control. The cell growth conditions of NPC-TW04 cells at 0, 12 and 24 h after scratching are shown in FIG. 4. The migration ability of NPC-TW04 cells was hindered when SOX5 gene was knocked-down.

Collectively, knocking-down of SOX5 in NPC cells was closely related to proliferation and migration of NPC cells from the experiments of MTT analysis and scratch migration assay. Knocking-down of SOX5 gene expression inhibited the proliferation and migration of NPC cells.

Further investigation on inhibition of Sparc protein in addition to knocking-down of SOX5 was performed to determine the interfering effects of Sparc on SOX5 knocking-down. After SOX5 shRNA containing plasmid was transfected into NPC-TW04 cells, 4 µg/ml and 16 µg/ml of anti-Sparc antibody were supplemented to the media, respectively, and cultivated for 2 days. The proliferation rate of NPC cells transfected with SOX5 shRNA was increased 48% after supplemented with 16 µg/ml of anti-Sparc antibody in comparison with those without the addition of anti-Sparc antibody. In another word, supplementation of anti-Sparc antibody could recover the proliferation ability hindered by SOX5 knocking-down, while supplementation of anti-Fgfr1 antibody showed no such function. It indicates that the function of SOX5 and SPARC genes in NPC cells is opposed. Namely, inhibition of the SOX5 gene blocked the dividing and migration ability of NPC cells, while inhibition of the SPARC gene increased dividing and migration ability of NPC cells.

Example 4

The Effects of Overexpression of SPARC on NPC Cells

The Sparc protein was abundant in the normal nasomucosal (NNM9) cell culture medium from the result of Western blotting in Example 3 (FIG. 2B), while very little in the NPC-TW04 cell culture medium. This phenomenon was consistent in the cell lysates (FIG. 5A). In another word, Sparc was abundant in the cell lysates of normal nasomucosal cells (NNM12 and NNM14), but could not be detected in cell lysates of the twelve NPC cell lines. Therefore, the Sparc proteins are inhibited significantly in NPC cells.

The effects of overexpression of SPARC on NPC cells and the SPARC related genes were studied since the Sparc proteins were inhibited significantly in NPC cells. To overexpress SPARC in NPC cells, a tetracycline-inducible expression vector pBIG2i containing SPARC gene was transfected into NPC-TW01 cells. Addition of 4 µg/ml of doxycycline (+Doxy group) into the culture medium for 24 h was performed to induce the overexpression of SPARC in NPC-TW01 cells. Cells transfected with pBIG2i plasmid containing no inserted gene (empty vector), or cells transfected with pBIG2i containing SPARC gene in the absence of doxycycline induction (-Doxy group) were served as control. Western blot analysis showed that the Sparc was induced to a large amount in the +Doxy group (FIG. 5B). Afterwards, nuclei in the +Doxy and -Doxy groups were detected by the DNA-binding fluorescent dye H33258 (FIG. 5C-a, FIG. 5C-b); which showed the cell numbers at the same time. Sparc proteins in cells of the -Doxy and +Doxy groups were also stained (FIG. 5C-c, FIG. 5C-d) using immunofluorescent staining method as described in Example 2. The addition of doxycycline to the NPC-TW01 cells showed Sparc expression from either Western blot analysis or immunostaining (FIGS. 5A and 5C-d). The biological functions of Sparc thus can be revealed in this cell model.

The cell functions such as cell doubling time, migration ability and invasion activity after overexpression of SPARC were determined in this cell model. The abovementioned MTT assay was carried out to determine cell doubling time. Doubling times of cells transfected with pBIG2i plasmid containing SPARC gene or containing no inserted gene (empty vector) were compared in the presence or in the absence of doxycycline (FIG. 6A). Overexpression of SPARC in NPC-TW01 cells allowed prolongation of cell doubling time for more than 4 h. Scratch migration assay was used to compare the NPC-TW01 cell migration ability in the presence or absence of doxycycline addition for SPARC overexpression. The cell growth conditions of NPC-TW01 cells at 0, 6 and 12 h after scratching are shown in FIG. 6B. The migration ability of NPC-TW01 cells was hindered when the SPARC gene was overexpressed. Together with the result of Example 4 that inhibition of the Sparc expression would affect the knocked-down effects of the SOX5 gene on cell division. In summary, the expression of the SPARC expression would affect the proliferation and migration ability of NPC cells. In another word, overexpression of the SPARC gene can hinder the proliferation and migration ability of NPC cells, while inhibition of the SPARC gene can promote the proliferation and migration ability of NPC cells.

Furthermore, the membrane invasion chamber system (MICS) was used to measure the effects of SPARC overexpression toward NPC cell line's invasion activity. A nitrocellulose membrane (24 wells of Falcon FluoroBlack insert system) of 8 µm diameter pores and coated with 50 µl/well matrigel (BD Biosciences) was placed between the upper and lower chambers of the Boyden chamber. Transmigration of cells across the membrane is regarded as an indicator of the invasive behavior of cells. Cell invasion was measured after cancer cells were plated on the top chamber for 24 h. The number of invasive cells from the SPARC overexpression group (NPC-TW01) was one tenth of that from the control group (without induction of doxycycline) (FIG. 7). Overexpression of SPARC could weaken the invasion activity of NPC cells significantly. Therefore, besides being a genetic marker, SPARC can also be a target gene in NPC therapy since it has obvious inhibiting effects in NPC proliferation, migration, and invasion.

The effect of SPARC overexpression on cancer related gene expressions such as MMP2, MMP9, RECK, TIMP-1, TIMP-2 and TIMP-4 was assessed with semi-quantitative RT-PCR in the present invention. The sample preparation of semi-quantitative RT-PC was the same as described in Q-RT-PCR of Example 1. cDNA preparation was mixed with PCR reagents, forward primer and reverse primer, followed by PCR reaction. Cycling parameters consisted of an initial denaturation step at 90° C. for 2 min, followed by 30 cycles of 94° C. for 30 sec, 55° C. for 30 sec, and 72° C. for 1 min, then extension at 72° C. for 7 min and terminated at 4° C. Amplified DNA products were aliquoted every 5 cycles and running in an agarose gel to confirm the linearity of PCR. FIG. 8A-a shows the amplified results of cancer related gene expressions including MMP2, MMP9, RECK, TIMP-1, TIMP-2 and TIMP-4. Among them, only mRNA of the RECK gene showed a 3-fold increase (FIG. 8A-b).

RECK gene is known to suppress tumor metastasis and invasion. Previous studies have demonstrated that RECK could inhibit metastasis of NPC. The mRNA of RECK increased when the SPARC gene was overexpressed. These findings indicate that RECK is the downstream gene of SPARC. The effect of SOX5 knocking-down on RECK mRNA expression was studied since the expression of the SPARC gene was increased when the SOX5 gene was knocked down. Q-RT-PCR analysis showed that the RECK mRNA increased around 2.44-fold in SOX5 knocked-down cells. In summary, the SOX5 gene is a major factor for regulation of NPC suppressor genes, which can down-regulate the SPARC gene. And the SPARC gene may act to up-regulate the downstream tumor suppressor genes, such as RECK to affect the formation of NPC. In other words, the effect of the SOX5 gene expression can be inhibited by increasing SPARC expression, resulting in increase of RECK expression to achieve the objective of inhibition of NPC progression.

Example 5

In Vivo Experiment

The invention used NOD SCID mouse to study the correlation of SOX5 and SPARC genes in vivo. NOD SCID mice were transplanted with human tumor cells to establish a xenograft model for studies regarding the tumor behavior, such as the metastatsis ability or the treatment strategy. First of all, NOD SCID mice were injected subcutaneously with NPC-TW04 cells transfected with pSM2C plasmid containing SOX5 shRNA ($5 \times 10^7$ SOX5 knocked-down NPC-TW04 cells), and compared with those injected with NPC-TW04 cells (without SOX5 knocking-down) or NPC-TW04 cells transfected with pSM2C plasmid containing no SOX5 shRNA. The weight of NPC xenograft tumor generated was decreased 5-fold in the NOD SCID mice injected with SOX5 knocked-down NPC-TW04 cells. (FIG. 9A). It is shown that the SOX5 gene indeed affected the growth of NPC xenograft. In addition, lung metastasis from NPC were found in 30% of mice injected with NPC-TW04 control cells (without SOX5 knocking-down), while no metastasis was found in mice injected with SOX5 knocking-down NPC-TW04 cells (data not shown). Collectively, the SOX5 gene may serve as an innovative target gene for NPC therapy.

In SPARC overexpression studies, NOD SCID mice were injected with transfected NPC-TW01 cells, where the plasmid transfected was a tetracycline-inducible expression vector pBIG2i containing the SPARC gene. Doxycycline was applied as an inducer for SPARC. The weight of NPC xenograft tumor generated was decreased more than 2.5-fold in the NOD SCID mice when SPARC overexpression was induced by doxycycline. (FIG. 9B). It is shown that overexpression of the SPARC gene inhibited the growth of NPC xenograft. Hematoxylin and Eosin staining (H&E staining) and immunostaining of xenograft sections revealed that Sparc was expressed in all tumor cells with doxycycline induction (FIG. 9C-b2), but not in the mice without doxycycline induction (FIG. 9C-a2). More fibroblasts and connective tissues but less blood vessels as well as the elevation of apoptasis were observed in SPARC overexpressed tumor (FIG. 9C-b1, FIG. 9C-b2). In addition, many visceral organs with serosal metastasis from NPC was found in 6 NOD SCID mice with no SPARC overexpression, while less number and small sizes of metastasis tumor was found in the other 6 NOD SCID mice with SPARC overexpression (data not shown). The apoptasis in NPC xenograft was also shown (FIG. 9C-b1). Collectively, the SPARC gene not only induces the apoptosis of NPC cells and inhibits the angiogenesis, but also act as a tumor suppressor gene to up-regulate other tumor suppressor genes such as RECK and the related factors of angiogenesis in the enhancement of NPC progression.

Example 6

Correlation Between Genes of SOX5 and Sparc as Well as Liver Cancer, Lung Cancer or Uterine Cervical Cancer The correlation between gene of SOX5 and/or SPARC as well as NPC was shown from the abovementioned studies. This experiment went a step further to study the correlation of SOX5 and/or SPARC and other cancers. mRNA of SOX5 and SPARC was determined with Q-RT-PCR in cells of normal nasomucosal cells (NNM), NPC cell lines, liver cancer cell lines of HepG2, Hep3B, and HuH7, lung cancer cell lines of PC13, uterine cervical cancer cell lines of Caski and HeLa, and oral cancer cell lines of CAL27, SAS, and Ca9-22. Results showed that mRNA levels of SOX5 were significantly increased in liver cancer cell lines of HepG2, Hep3B, and HuH7, lung cancer cell lines of PC13, and uterine cervical cancer cell lines of HeLa after compared to that of normal nasomucosal cells (FIG. 10A). While mRNA levels of SPARC were almost not detected in liver cancer cell lines of Hep3B, lung cancer cell lines of PC13, and uterine cervical cancer cell lines of Caski after compared to that of normal nasomucosal cells (FIG. 10B). The detection of SOX5 and/or SPARC genes can also be used as genetic markers for the prognosis of liver cancer, lung cancers and uterine cervical cancer.

On the other hand, high SOX5 expression and low SPARC expression were found on cell lines from NPC, liver cancer, lung cancer, and some of the uterine cervical cancer cell lines. From the abovementioned examples, the detection of SOX5 and/or SPARC genes can be a prognosis indicator for NPC; SOX5 knocking-down or SPARC overexpression can be applied in inhibiting the enhancement of NPC progression. Namely, SOX5 and/or SPARC genes can be used as target genes for the prognosis of NPC or NPC therapy. To further study the application of SOX5 and/or SPARC genes in liver, lung, and uterine cervical cancers, the present invention studied the biological function of SPARC in liver cancer cell lines HepG2. The method of overexpressing SPARC in HepG2 cells is the same as described in NPC cells from Example 4. The doubling time and invasion activity of SPARC overexpressed HepG2 cells as described in Example 3. Overexpression of SPARC in HepG2 cells allowed decrease of cell proliferation rate when determined with MTT assay (FIG. 11A). The cell proliferation rate was decreased 25% and 27% at the second cultivation day, and decreased 30% and 32.5% at the third day after addition of doxycycline at the concentration of 2 μg/ml or 4 μg/ml, respectively, in comparison with the no SPARC overexpression group. Overexpression of the SPARC gene can hinder the invasion ability of the liver cancer cells. The invasion activity of SPARC overexpressed cells was decreased 13% and 50% after addition of doxycycline at the concentration of 2 μg/ml or 4 μg/ml, respectively, in comparison with the no SPARC overexpression group (FIG. 11B). Overexpression of the SPARC gene in both the liver cancer cells and NPC cells can weaken the invasion activity of cancer cells.

The biological function of SPARC overexpression was studied through in vivo experiment of NOD SCID mice as described in Example 5. Sizes of hepatoma xenograft tumors in mice were smaller when overexpression of the SPARC gene was induced by doxycycline (FIG. 11C). Collectively, the results of liver cancer cells were similar to those of NPC cells. The SPARC gene can serve as a target gene not only for NPC therapy, but also for liver cancer therapy. The abovementioned examples also proved that SOX5 gene can serve as a target gene for NPC therapy, and both SOX5 and/or SPARC genes can be the prognosis indicators of NPC, liver cancer, lung cancer, and uterine cervical cancer. In summary, both SOX5 and/or SPARC genes can serve as the target genes for the prognosis and cancer therapy including NPC liver cancer, lung cancer, and uterine cervical cancer.

The above embodiments are described only for preferred examples. Those examples above should not, however, be considered to limit the scope of the invention, it is contemplated that modifications will readily occur to those skilled in the art, which modifications will be within the spirit of the invention and the scope of the appended claims.

What is claimed is:

1. A method for predicting a risk of distant metastasis and the poor prognosis in a cancer patient, comprising:
    obtaining a sample from the patient;
    evaluating the expression levels of the SOX5 genetic marker in the sample; and
    comparing the expression levels of genetic markers in the sample with a non-cancerous sample;
    wherein the patient is determined to have the risk of distant metastasis or poor prognosis when the expression level of SOX5 is higher than that of non-cancerous sample;
    wherein the cancer is nasopharyngeal cancer, liver cancer or uterine cervical cancer.

2. The method as claimed in claim 1, wherein the sample is a tissue.

3. The method as claimed in claim 1, wherein the method comprises evaluating the expressed protein levels encoded from the SOX5 genetic marker.

4. The method as claimed in claim 1, wherein the method comprises evaluating the expressed mRNA levels of the SOX5 genetic marker.

5. The method as claimed in claim 1, wherein the cancer is nasopharyngeal cancer.

6. The method as claimed in claim 1, wherein the cancer is liver cancer.

7. The method as claimed in claim 1, wherein the cancer is uterine cervical cancer.

* * * * *